United States Patent
Carlson

(10) Patent No.: US 8,472,112 B2
(45) Date of Patent: *Jun. 25, 2013

(54) STABLE INFRARED FILMS

(75) Inventor: Steven Allen Carlson, Cambridge, MA (US)

(73) Assignee: Optodot Corporation, Watertown, MA (US)

( * ) Notice: Subject to any disclaimer, the term of this patent is extended or adjusted under 35 U.S.C. 154(b) by 283 days.

This patent is subject to a terminal disclaimer.

(21) Appl. No.: 12/589,773

(22) Filed: Oct. 28, 2009

(65) Prior Publication Data

US 2010/0104817 A1   Apr. 29, 2010

Related U.S. Application Data

(60) Provisional application No. 61/197,553, filed on Oct. 28, 2008.

(51) Int. Cl.
*F21V 9/04* (2006.01)

(52) U.S. Cl.
USPC ................................ 359/350; 428/195.1

(58) Field of Classification Search
USPC ...................................... 428/195.1; 359/350
See application file for complete search history.

(56) References Cited

U.S. PATENT DOCUMENTS

| 5,061,341 | A | 10/1991 | Klidal et al. | |
| 5,109,064 | A * | 4/1992 | Wakabayashi et al. | ....... 525/100 |
| 6,316,264 | B1 | 11/2001 | Corey et al. | |
| 7,601,544 | B2 | 10/2009 | Rehm | |
| 2005/0041281 | A1 | 2/2005 | Aoyama et al. | |
| 2006/0121392 | A1* | 6/2006 | Nakatsugawa | ........... 430/270.17 |
| 2007/0097510 | A1 | 5/2007 | Carlson | |
| 2008/0136160 | A1 | 6/2008 | Leenders | |
| 2008/0138289 | A1 | 6/2008 | Goronkin et al. | |

FOREIGN PATENT DOCUMENTS

WO   PCT/US09/05850   1/2010

* cited by examiner

*Primary Examiner* — Mark Ruthkosky
*Assistant Examiner* — Ian Rummel
(74) *Attorney, Agent, or Firm* — Finch & Maloney PLLC

(57) ABSTRACT

Provided are infrared films comprising a substrate, a layer of an aminium radical cation compound in a crystalline state and an organic polymer selected from the group consisting of a divinyl ether polymer, a fluoropolymer, and a silicone polymer, and, optionally, a water repellent layer overlying the layer of the aminium compound. Such infrared films are stable in their optical properties and useful for security markings, test strips for analysis of fluids, and other optical articles for detection in the infrared. Also provided are methods for making such infrared films.

34 Claims, No Drawings

STABLE INFRARED FILMS

RELATED APPLICATIONS

This application claims the benefit of U.S. Provisional Patent Application No. 61/197,553, filed Oct. 28, 2008, entitled "Stable Infrared Films," by Carlson, which is incorporated herein by reference for all purposes.

FIELD OF THE INVENTION

The present invention relates generally to the field of infrared films, and particularly, pertains to infrared films that are stable to heat and light and are water repellent and that are very low in color while providing strong infrared absorption. More specifically, this invention pertains to infrared films comprising at least one layer that comprises an aminium free radical cation compound in a crystalline state and an organic polymer selected from the group consisting of a divinyl ether polymer, a fluoropolymer, and a silicone polymer. This invention also pertains to test strips for analysis of fluids, security markings, and other optical articles comprising the infrared films of this invention and to methods of making a test strip, security marking, or other optical article by utilizing the infrared films of the present invention.

The subject matter disclosed and claimed herein was developed under a joint research agreement between Optodot Corporation and Madico, Inc.

BACKGROUND OF THE INVENTION

Throughout this application, various patents and published patent applications are referred to by an identifying citation. The disclosures of the patents and published patent applications referenced in this application are hereby incorporated by reference into the present disclosure to more fully describe the state of the art to which this invention pertains.

Some products, such as security markings and test strips for the analysis of fluid samples, would benefit from colorless or nearly colorless layers that have strong absorption in the infrared region so that the products can be read by an infrared scanner or camera but do not provide enough of a visible image to be detected by humans or a visible scanner or camera. For example, U.S. Pat. No. 6,316,264 to Corey et al. describes a test strip for determining the presence or concentration of an unknown or a constituent in a liquid test sample, where the test strip comprises an infrared layer that has a detectable response in the infrared region but does not interfere with the response of the test strip in the visible region. Also, for example, U.S. Pat. Nos. 6,381,059; 6,589,451; and 7,151,626, all to Carlson, describe infrared layers for security markings that comprise an aminium radical cation compound and are capable of being detected in the infrared region while being invisible or nearly invisible to the human eye or to detection by a visible scanner.

It would be advantageous if such infrared layers were highly stable in the intensity level of their infrared absorption and in their level of visible coloration to light, heat, and upon extended periods of storage under ambient conditions and, for certain applications that involve direct contact with aqueous fluids such as test strips for fluid samples, were water repellent so the fluids do not cover or degrade the infrared layer.

SUMMARY OF THE INVENTION

This invention pertains to stable infrared films that are very low in color while providing strong infrared absorption and preferably are water repellent.

One aspect of this invention pertains to an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer. In one embodiment, the aminium radical cation compound is a salt of an aminium radical cation, wherein the anion of the salt is selected from the group consisting of hexafluoroantimonate and hexafluorophosphate. In one embodiment, the aminium radical cation compound is a salt of a tetrakis(phenyl)-1,4-benzenediamine radical cation. In one embodiment, the aminium radical cation compound is a salt of a tris(phenyl)-aminium radical cation.

In one embodiment of the infrared films of the present invention, the at least one layer of the infrared film has an absorption peak in the range of 800 to 900 nm. In one embodiment, the absorption of the at least one layer of the infrared film in the range of 420 to 680 nm is less than 20% of the absorption at the absorption peak in the range of 800 to 900 nm and, preferably, is less than 10% of the absorption at the absorption peak in the range of 800 to 900 nm.

Another aspect of the infrared films of this invention pertains to the at least one layer comprising an aminium radical cation compound in a crystalline state and a divinyl ether polymer selected from the group of polymers of the divinyl ethers of ethylene glycol, diethylene glycol, triethylene glycol, tetraethylene glycol, 1,4-butanediol, and 1,4-cyclohexanedimethanol. In one embodiment, the at least one layer comprising the aminium radical cation compound and the divinyl ether polymer further comprises an aliphatic urethane. In one embodiment, the at least one layer comprises a fluoropolymer. In one embodiment, the at least one layer comprises a fluoropolymer and an aliphatic urethane. In one embodiment, the at least one layer comprises a silicone polymer. In one embodiment, the at least one layer comprises a silicone polymer and an aliphatic urethane.

Another aspect of the infrared films of the present invention relates to the substrate comprising a reflective opaque substrate, preferably a white polyester film.

Still another aspect of the infrared films of this invention pertains to the infrared film comprising a water repellent layer overlying the at least one layer comprising the aminium radical cation compound. In one embodiment, the water repellent layer comprises a fluoropolymer. In one embodiment, the water repellent layer comprises a silicone polymer, preferably a crosslinked silicone polymer.

One aspect of the present invention pertains to a test strip for analysis of fluids, which test strip comprises an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer. In one embodiment, the substrate is a white polyester film, the at least one layer comprises an aminium radical cation compound in a crystalline state, an aliphatic urethane, and a divinyl ether polymer, and a water repellent second layer overlying the at least one layer.

Another aspect of this invention pertains to a security marking, which security marking comprises an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer.

Still another aspect of this invention pertains to an optical article, which optical article comprises an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer. In one embodiment, the infrared film comprises a laser imaged pattern on at least one of the at least one layer comprising the aminium radical cation compound, wherein the infrared absorption of the aminium radical cation compound is changed by exposure to a laser and the laser imaged pattern is readable in the infrared region. In one embodiment, the laser imaged pattern is readable in the eye-safe region above 1400 nm.

Another aspect of the present invention relates to methods of making an infrared film, wherein the method comprises the steps of providing (a) a substrate, (b) a first layer overlying the substrate, wherein the first layer comprises an aminium radical cation compound in a crystalline state and an organic polymer selected from the group consisting of a divinyl ether polymer, a fluoropolymer, and a silicone polymer, and (c) a second water repellent layer overlying the first layer. In one embodiment, the second layer comprises a fluoropolymer. In one embodiment, the second layer comprises a silicone polymer. In one embodiment, the substrate is a reflective opaque substrate, preferably a white polyester film.

As will be appreciated by one of skill in the art, features of one aspect or embodiment of the invention are also applicable to other aspects or embodiments of the invention.

DETAILED DESCRIPTION OF THE INVENTION

Organic Free Radical Compounds

The term "organic free radical compound," as used herein, pertains to an organic compound which comprises at least one free unpaired electron on an atom, such as, for example, a carbon atom, a nitrogen atom, or an oxygen atom, in the ground state of the organic compound. Suitable organic free radical compounds for the infrared layers, test strips, security marking systems, and optical articles of the present invention include salts of organic free radical cations. For purposes of brevity, the terms "organic free radical cation," "organic radical cation," and "radical cation" are used interchangeably herein. The word "cation," as used herein, pertains to a positively charged atom in a molecule, such as, for example, a positively charged nitrogen atom. It should be noted that the free unpaired electron and the positive charges of the organic free radical compounds may be localized on a single atom or shared among more than one atom.

Examples of suitable salts of organic free radical cations for the infrared layers, test strips, security marking systems, and optical articles of this invention include, but are not limited to, salts of aminium radical cation compounds, such as, for example, tris(p-dibutylaminophenyl) aminium hexafluoroantimonate, which is commercially available as IR-99, a tradename for a dye available from Sperian Protection, Smithfield, R.I. Another suitable salt of an aminium radical cation compound is IR-165, which is a tradename for a dye available from Sperian Protection, Smithfield, R.I. IR-165 is the hexafluoroantimonate salt of a tetrakis(phenyl)-1,4-benzenediamine radical cation.

Coatings comprising aminium radical cation compounds have been found to exhibit high levels of reflectance in the infrared, as described in U.S. Pat. No. 7,151,626 to Carlson and in U.S. Pat. Pub. Applic. No. 20070097510, to Carlson et al. Layers comprising IR-165 type compounds have a much lower absorption in the 400 to 700 nm wavelength region of the visible than do IR-99 type compounds for a comparable amount of infrared blocking, and thus are preferred for product applications where strong infrared absorption and blocking is desired with no or very little visible color.

The terms "infrared" and "infrared region" are used interchangeably herein and pertain to wavelengths form 700 nm to 2500 nm. The terms "visible wavelength region," "visible wavelength," visible region," and "visible" are used interchangeably herein and pertain to wavelengths from 400 nm to 700 nm.

Suitable salts of organic radical cation compounds for the infrared layers of this invention include, but are not limited to, salts of an aminium radical cation compound. The choice of the counteranion for the salt depends on a variety of factors such as, for example, the ease and cost of applying the infrared layer and the required stability of the infrared layers where the organic radical cation salt is utilized, against degradation by oxygen, moisture, and photon exposures.

Chart 1 shows the chemical structure of IR-99, a representative free radical compound for the infrared blocking layers of this invention. IR-99 is an example of a salt of a tris(4-dialkylaminophenyl) aminium radical cation.

Chart 1. IR-99 for Infrared Blocking Layers

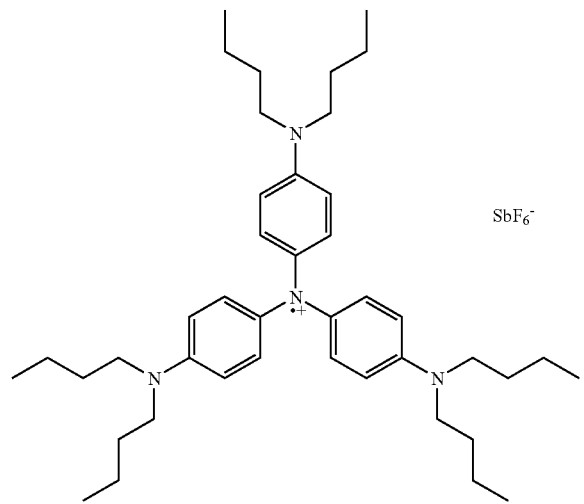

It can be seen in Chart 1 that IR-99 is an organic free radical compound with a single free electron shown on one of the nitrogen atoms. It is present in a salt form with a hexafluoroantimonate anion in this case.

In one embodiment of the infrared films of this invention, the aminium radical cation compound is a salt of an aminium radical cation, wherein the anion of the salt is selected from the group consisting of hexafluoroantimone and hexafluorophosphate. In one embodiment, the aminium radical cation compound is a salt of a tetrakis(phenyl)-1,4-benzenediamine radical cation. In one embodiment, the aminium radical cation compound is a salt of a tris(phenyl)-aminium radical cation.

Infrared Films for Security Marking Systems, Test Strips, and Optical Articles

This invention pertains to stable infrared films that are very low in color while providing strong infrared absorption and preferably are water repellent. As used herein, the words "film" or "films" pertain to any article or product that comprises at least one layer that is on a clear or an opaque substrate such as, for example, a white polyethylene terephthalate, herein called polyester, film, a clear polyester film, a white polystyrene film, a clear polypropylene film, and a white polyvinyl chloride (PVC) film. For example, the infrared films of this invention include configurations where a plastic or polymer layer is coated or laminated on a paper or a metal or another plastic film.

One aspect of this invention pertains to an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer. In one embodiment, the aminium radical cation compound is a salt of an aminium radical cation, wherein the anion of the salt is selected from the group consisting of hexafluoroantimonate and hexafluorophosphate. In one embodiment, the aminium radical cation compound is a salt of a tetrakis(phenyl)-1,4-benzenediamine radical cation. In one embodiment, the aminium radical cation compound is a salt of a tris(phenyl)-aminium radical cation.

The crystalline state of the aminium radical cation compound provides additional stability to the optical properties of the infrared film under storage conditions and exposure to heat, light, and moisture. The crystalline state of the aminium radical cation compound means that the aminium radical cation compound has formed crystals in the layer. These crystals can be observed under a high power microscope or, in the case of clear transparent infrared films, can also be seen by an increase in the percent haze due to the formation of crystals. The crystalline state of the aminium radical cation compound, such as IR-165, can be formed by extended heating of the layer at high temperatures, such as 130° C., or by including a high boiling solvent with limited solubility for the aminium radical cation compound, such as 2,4-pentanedione, in the coating formulation. This high boiling solvent causes the aminium radical cation compound to precipitate out or crystallize in the last stages of drying, thereby forming the aminium radical cation compound in a crystalline state in the layer of the infrared film.

In one embodiment of the infrared films of the present invention, the at least one layer of the infrared film has an absorption peak in the range of 800 to 900 nm. This is a typical infrared wavelength range for detection by infrared scanners or cameras. In one embodiment, the absorption of the at least one layer of the infrared film in the range of 420 to 680 nm is less than 20% of the absorption at the absorption peak in the range of 800 to 900 nm and, preferably, is less than 10% of the absorption at the absorption peak in the range of 800 to 900 nm. IR-165 in a crystalline state is particularly suitable for meeting and maintaining these desired absorption properties.

Another aspect of the infrared films of this invention pertains to the at least one layer comprising an aminium radical cation compound in a crystalline state and a divinyl ether polymer selected from the group of polymers of the divinyl ethers of ethylene glycol, diethylene glycol, triethylene glycol, tetraethylene glycol, 1,4-butanediol, and 1,4-cyclohexanedimethanol. While not wishing to be bound by a particular theory, it is believed that the aminium radical cation compound with its cationic groups catalyzes the cationic polymerization of the monomer of divinyl ether compounds to form a polymer of the divinyl ether compounds. One approach to provide the divinyl ether polymer is to include the monomer of the divinyl ether compound in the coating formulation of the aminium radical cation compound and organic solvents, such as 2-butanone and cyclohexanone, to make the layer and retaining a portion of the divinyl ether compound in a polymer state after drying and heating the layer, while some of the monomer is volatilized and removed during the drying and heating. In one embodiment, the at least one layer comprising the aminium radical cation compound and the divinyl ether polymer further comprises an aliphatic urethane such as, for example, CA-128, the tradename for an aliphatic urethane available from Huntsman Corporation. The aliphatic urethane polymer adds cohesive and adhesive strength to the layer. In one embodiment, the at least one layer further comprises a fluoropolymer such as, for example, Kynar 9037, a tradename for a polyvinylidene fluoride polymer available from Dupont Corporation, Wilmington, Del. The fluoropolymer adds water repellency and resistance to moisture that increases the stability of the layer. The fluoropolymer also increases the flow properties and uniformity of the coating of the layer. In one embodiment, the at least one layer further comprises a fluoropolymer and an aliphatic urethane. In one embodiment, the at least one layer further comprises a silicone polymer such as a dimethylpolysiloxane polymer. The silicone polymer adds water repellency and resistance to moisture that increases the stability of the layer. The silicone polymer also increases the flow properties and uniformity of the coating of the layer. In one embodiment, the at least one layer further comprises a silicone polymer and an aliphatic urethane.

Another aspect of the infrared films of the present invention relates to the substrate comprising a reflective opaque substrate, preferably a white polyester film such as, for example, MELINEX 339, a tradename for a polyester film from Dupont Teijin Corporation, Hopewell, Va., that comprises barium sulfate pigment particles that reflect infrared and visible radiation. The reflective opaque substrate is useful in providing a background of high infrared reflectance against which the infrared film with its blocking of the infrared radiation in the initial pass through the layer comprising the aminium radical cation compound and in the return pass through this layer after reflecting off of the substrate, can be readily detected by an infrared scanner or camera, even at very low amounts of the aminium compound in the layer, such as 0.05 g/m$^2$ and lower.

Still another aspect of the infrared films of this invention pertains to the infrared film comprising a water repellent layer overlying the at least one layer comprising the aminium radical cation compound. This water repellency is useful in increasing the stability against degradation by water and in repelling any undesired aqueous fluids off of the surface of the infrared film to avoid any interference with the detection in the infrared region or to prevent any undesired detection in the visible region. The level of water repellency is at least a contact angle of 60° for a water drop on the water repellent layer, and preferably at least a contact angle of 90°. In one embodiment, the water repellent layer comprises a fluoropolymer, such as a polyvinylidene fluoride polymer. In one embodiment, the water repellent layer comprises a silicone polymer, preferably a crosslinkable silicone polymer such as a polysiloxane with Si—H groups that forms a crosslinked silicone polymer in the water repellent layer.

One aspect of the present invention pertains to a test strip for analysis of fluids, which test strip comprises an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer. In one embodiment, the substrate is a white polyester film, the at least one layer comprises an aminium radical cation compound in a crystalline state, an aliphatic urethane, and a divinyl ether polymer, and a second layer overlying the at least one layer, wherein the second layer comprises a silicone polymer.

Another aspect of this invention pertains to a security marking, which security marking comprises an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer.

Still another aspect of this invention pertains to an optical article, which optical article comprises an infrared film comprising a substrate and at least one layer, wherein the at least one layer comprises an aminium radical cation compound in a crystalline state and an organic polymer selected from the group consisting of a divinyl ether polymer, a fluoropolymer, and a silicone polymer. Optical articles include, but are not limited to, test strips for analysis of fluids, security markings and security marking systems, and other applications where the article may be detected or utilized optically in the infrared region. In one embodiment, the infrared film comprises a laser imaged pattern on at least one of the at least one layer comprising the aminium radical cation compound, wherein the infrared absorption of the aminium radical cation compound has been changed by exposure to a laser and the laser imaged pattern is readable in the infrared region. Typically, the laser is an infrared laser, such as, for example, a semiconductor diode laser emitting at 830 nm or a YAG laser emitting at 1065 nm. In one embodiment, the laser imaged pattern is readable in the eye-safe region above 1400 nm. This broad infrared range for detection from 700 nm to 1600 nm, and higher depending on the choice of the aminium radical cation compound, is useful in providing an option for reading the infrared film at an eye-safe wavelength so that, for example, it could be read with an infrared laser device at a store checkout counter or in a crowded room without concern about harming any of the people present.

Another aspect of the present invention relates to methods of making an infrared film, wherein the method comprises the steps of providing (a) a substrate, (b) a first layer overlying the substrate, wherein the first layer comprises an aminium radical cation compound in a crystalline state and an organic polymer selected from the group consisting of a divinyl ether polymer, a fluoropolymer, and a silicone polymer, and (c) a second water repellent layer overlying the first layer. In one embodiment, the second layer comprises a fluoropolymer. In one embodiment, the second layer comprises a silicone polymer. In one embodiment, the substrate is a reflective opaque substrate, preferably a white polyester film.

While the invention has been described in detail and with reference to specific and general embodiments thereof, it will be apparent to one skilled in the art that various changes and modifications can be made therein without departing from the spirit and scope thereof.

The invention claimed is:

1. An infrared film comprising a substrate and at least one layer, wherein said at least one layer comprises an aminium radical cation dye in a crystalline state and an organic polymer selected from the group consisting of a divinyl ether polymer, a fluoropolymer, and a silicone polymer, wherein said aminium radical cation dye has formed crystals in said at least one layer.

2. The infrared film of claim 1, wherein said aminium radical cation dye is a salt of an aminium radical cation, wherein the anion of said salt is selected from the group consisting of hexafluoroantimonate and hexafluorophosphate.

3. The infrared film of claim 1, wherein said aminium radical cation compound is a salt of a tetrakis(phenyl)-1,4-benzenediamine radical cation.

4. The infrared film of claim 1, wherein said aminium radical cation dye is a salt of a tris(phenyl)-aminium radical cation.

5. The infrared film of claim 1, wherein said at least one layer of said infrared film has an absorption peak in the range of 800 to 900 nm.

6. The infrared film of claim 5, wherein the absorption of said at least one layer of said infrared film in the range of 420 to 680 nm is less than 20% of the absorption at said absorption peak in the range of 800 to 900 nm.

7. The infrared film of claim 5, wherein the absorption of said at least one layer of said infrared film in the range of 420 to 680 nm is less than 10% of the absorption at said absorption peak in the range of 830 to 860 nm.

8. The infrared film of claim 1, wherein said divinyl ether polymer is selected from the group of polymers of the divinyl ethers of ethylene glycol, diethylene glycol, triethylene glycol, tetraethylene glycol, 1,4-butanediol, and 1,4-cyclohexanedimethanol.

9. The infrared film of claim 8, wherein said at least one layer comprising said aminium radical cation dye and said divinyl ether polymer further comprises an aliphatic urethane polymer.

10. The infrared film of claim 1, wherein said fluoropolymer is a polyvinylidene fluoride.

11. The infrared film of claim 10, wherein said at least one layer comprising said aminium radical cation dye and said polyvinylidene fluoride further comprises an aliphatic urethane polymer.

12. The infrared film of claim 1, wherein said silicone polymer is a dimethylpolysiloxane polymer.

13. The infrared film of claim 12, wherein said at least one layer comprising said aminium radical cation dye and said dimethylpolysiloxane polymer further comprises an aliphatic urethane polymer.

14. The infrared film of claim 1, wherein said at least one layer comprising said aminium radical cation dye comprises a divinyl ether polymer and a fluoropolymer.

15. The infrared film of claim 14, wherein said at least one layer comprising said aminium radical cation dye further comprises an aliphatic urethane polymer.

16. The infrared film of claim 1, wherein said at least one layer comprising said aminium radical cation dye comprises a divinyl ether polymer and a silicone polymer.

17. The infrared film of claim 16, wherein said at least one layer comprising said aminium radical cation dye further comprises an aliphatic urethane polymer.

18. The infrared film of claim 1, wherein said substrate comprises a reflective opaque substrate.

19. The infrared film of claim 1, wherein said substrate is a white polyester film.

20. The infrared film of claim 1, wherein said infrared film comprises a water repellent layer overlying said at least one layer comprising said aminium radical cation dye, wherein a water drop on said water repellent layer has at least a contact angle of 90°.

21. The infrared film of claim 20, wherein said water repellent layer comprises a fluoropolymer.

22. The infrared film of claim 20, wherein said water repellent layer comprises a silicone polymer.

23. The infrared film of claim 22, wherein said silicone polymer of said water repellent layer is a crosslinked silicone polymer.

24. A test strip for analysis of fluids, wherein said test strip comprises said infrared film of claim 1.

25. A test strip for analysis of fluids, wherein said test strip comprises an infrared film comprising:
   a. a white polyester film;
   b. a first layer comprising an aminium radical cation dye in a crystalline state, an aliphatic urethane polymer, and a divinyl ether polymer;
   c. a second layer overlying said first layer, wherein said second layer comprises a silicone polymer,
   wherein said aminium radical cation dye has formed crystals in said first layer, and wherein a water drop on said second layer has at least a contact angle of 90°.

26. A security marking, wherein said security marking comprises said infrared film of claim 1.

27. An optical article, wherein said optical article comprises said infrared film of claim 1.

28. The optical article of claim 27, wherein said infrared film comprises a laser imaged pattern on at least one of said at least one layer comprising said aminium radical cation dye, wherein the infrared absorption of said aminium radical cation dye has been changed by exposure to a laser and said laser imaged pattern is readable in the infrared region.

29. The optical article of claim 28, wherein said laser imaged pattern is readable in the eye-safe region above 1400 nm.

30. A method of making an infrared film, wherein said method comprises the steps of providing:
   a. a substrate,
   b. a first layer overlying said substrate, wherein said first layer comprises an aminium radical cation dye in a crystalline state and an organic polymer selected from the group consisting of a divinyl ether polymer, a fluoropolymer, and a silicone polymer;
   c. a water repellent second layer overlying said first layer wherein said aminium radical cation dye has formed crystals in said first layer, and wherein a water drop on said second layer has at least a contact angle of 90°.

31. The method of claim 30, wherein said second layer comprises a fluoropolymer.

32. The method of claim 30, wherein said second layer comprises a silicone polymer.

33. The method of claim 30, wherein said substrate is a reflective opaque substrate.

34. The method of claim 33, wherein said reflective opaque substrate is a white polyester film.

* * * * *